United States Patent [19]

Green, II et al.

[11] Patent Number: 5,288,753
[45] Date of Patent: Feb. 22, 1994

[54] METHOD OF CONTROLLING ANIMAL AND FUNGAL PESTS WITH OLIGOMERIC THIOCARBONATES

[75] Inventors: James A. Green, II, Chino; Donald C. Young, Fullerton, both of Calif.

[73] Assignee: Union Oil Company of California, Los Angeles, Calif.

[21] Appl. No.: 458,283

[22] Filed: Dec. 28, 1989

[51] Int. Cl.$^5$ .................... A01N 31/02; A01N 37/02; A01N 37/36; C07C 329/02; C07C 329/12

[52] U.S. Cl. .................... 514/512; 424/703; 560/302; 562/1; 562/26; 562/886; 558/244; 558/245; 514/553; 514/554

[58] Field of Search ............ 558/244, 245; 560/302; 514/512, 553, 554; 562/1, 26, 886; 424/703

[56] References Cited

U.S. PATENT DOCUMENTS

| | | | |
|---|---|---|---|
| 2,268,382 | 12/1941 | Cloud et al. | 558/244 |
| 2,615,804 | 10/1952 | Stewart et al. | 558/244 X |
| 2,770,638 | 11/1956 | Giolito et al. | 558/244 |
| 3,154,401 | 10/1964 | Van Den Boogaart | 558/244 X |
| 3,892,741 | 7/1975 | Taylor | 558/244 |
| 4,476,113 | 10/1984 | Young et al. | 558/244 X |
| 4,726,144 | 2/1988 | Young et al. | 424/161 |

OTHER PUBLICATIONS

Jeroschewski et al, Chemical Abstracts, vol. 93, #33855f (1980).
Silber et al, Chemical Abstracts, vol. 83, #141155c (1975).
"Carbon Sulfides and Their Inorganic and Complex Chemistry," by G. Gattow and W. Behrendt, *Topics in Sulfur Chemistry*, vol. 2, Edited by A. Senning, Georg Thieme Publishers, Stuttgart 1977.

*Primary Examiner*—Floyd D. Higel
*Attorney, Agent, or Firm*—Gregory F. Wirzbicki; Charles L. Hartman; Michael H. Laird

[57] ABSTRACT

Oligomeric thiocarbonates such as hexathiodicarbonate salts and thioesters are used as pesticides and preservatives. Certain oligomeric thiocarbonate salts, notably quaternary ammonium hexathiodicarbonates, are prepared. The compounds are stabilized with added base and/or sulfide.

34 Claims, No Drawings

METHOD OF CONTROLLING ANIMAL AND FUNGAL PESTS WITH OLIGOMERIC THIOCARBONATES

TECHNICAL FIELD

This invention relates to the field of thiocarbonates and, in particular, to oligomeric thiocarbonates, methods of making them, and their use as pesticides and preservatives.

INTRODUCTION

Compounds containing the structural units

(trithiocarbonate)

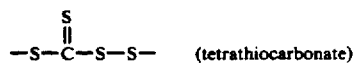
(tetrathiocarbonate)

have been found useful for a number of purposes. The chemistry of tri- and tetrathiocarbonates has been studied in some detail. See, for example, O'Donoghue and Kahan, Journal of the Chemical Society, Vol 89(II), pages 1812-1818 (1906); Yeoman, Journal of the Chemical Society, Vol 119, pages 38-54 (1921); Mills and Robinson, Journal of the Chemical Society Vol. 128(II), pages 2236-2332 (1928) and by Stone et al in U.S. Pat. No. 2,893,835.

When two mols of a hydroxide base MOH (wherein the cation M is ammonium, alkali metal, or alkaline earth metal ion), and one mol each of hydrogen sulfide, sulfur, and carbon disulfide are combined in a suitable solvent, the product is the tetrathiocarbonate salt $M_2CS_4$ as shown in general equation (1)

$$2MOH + H_2S + S + CS_2 \rightarrow M_2CS_4 + 2 H_2O \qquad (1)$$

The tetrathiocarbonate salt comprises one mol of bound carbon disulfide. Such tetrathiocarbonate salts and methods of making and using them have been described in our U.S. Pat. Nos. 4,476,113, 4,551,167, and 4,726,144, which are incorporated herein by reference in their entirety.

Physical and chemical properties of thiocarbonates and a number of methods for making them are summarized in "Carbon Sulfides and their Inorganic and Complex Chemistry" by G. Gattow and W. Behrendt, Volume 2 of "Topics in Sulfur Chemistry" A. Senning, Editor, George Thieme Publishers, Stuttgart, 1977, starting at page 154. A method of making dialkyl hexathiodicarbonate is described. At page 176, bis(tetramethylammonium) hexathiodicarbonate solvated with carbon disulfide is described. The compound, $[(H_3C)_4N]_2C_2S_6 \cdot \frac{1}{2}CS_2$, is said to crystallize from a solution of tetramethylammonium trithiocarbonate in methanol and carbon disulfide.

SUMMARY OF THE INVENTION

This invention comprises methods of using oligomeric thiocarbonates, processes for making certain oligomeric thiocarbonates, and certain novel oligomeric thiocarbonates.

Oligomeric thiocarbonates release carbon disulfide, an effective fumigant, upon decomposition. They can be used as pesticides for the treatment of enclosed spaces, agricultural soils, trees, and crops, and as preservatives for stored cellulosic materials such as wood chips and agricultural products They are especially useful as soil fumigants for the control of soil-borne pests such as nematodes and fungi.

As used herein, the term "oligomeric thiocarbonate" means any chemical compound containing the structural unit

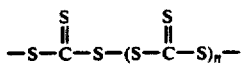

wherein n is a positive integer, preferably from 1 to about 5, and most preferably 1. This structural unit shall be referred to herein as an "oligomeric thiocarbonate unit." When n is 1, the structural unit is a hexathiodicarbonate unit, having the structural formula

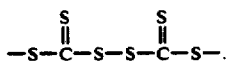

The oligomeric thiocarbonate structural unit can be present in chemical compounds made or used in accordance with this invention as, for example, an anion of a salt; an acidic part of a thioester, thioamide, xanthate, or sulfenyl compound; or a ligand of a coordination compound, chelate, or other complex.

This invention provides novel processes for making certain oligomeric thiocarbonates by reacting hydrogen sulfide and a strong hydroxide base ZOH (or the corresponding sulfide $Z_2S$) with sulfur and carbon disulfide. In the novel processes, Z is a bulky cation, preferably at least as bulky as a tetramethylammonium ion, sufficient to result in the formation of a reaction product comprising an oligomeric thiocarbonate structural unit. Certain novel oligomeric thiocarbonates can be made by the novel processes disclosed herein. preferred among these are quaternary ammonium hexathiodicarbonates wherein at least one quaternary ammonium ion comprises at least 5 carbon atoms.

DETAILED DESCRIPTION OF THE INVENTION

The present invention provides methods of using compositions of matter comprising oligomeric thiocarbonates. Any oligomeric thiocarbonate compound, i.e., any compound comprising the oligomeric thiocarbonate structural unit, can be used in accordance with this invention. Such compounds can be represented by the structural formula

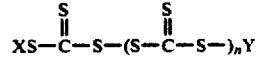

wherein n is an integer of at least 1, preferably from 1 to about 5, most preferably 1, and X and Y independently are any organic or inorganic groups. As shown by the formula, an oligomeric thiocarbonate comprises two or more repeating —$CS_3$— units joined by sulfur-sulfur bonds; a dimer thiocarbonate, for example, contains two —$CS_3$— units (n is 1), a trimer thiocarbonate contains three —$CS_3$— units (n is 2), and so on. The term "group" as used throughout the specification and the claims is intended to mean any single atom as well as any assemblage of atoms, including organic and inorganic cations as well as neutral or covalently bonded radicals. For example, a metal ion, a halogen atom, hydrogen, an ethyl radical, a benzyl radical, and a tetraethylammonium ion are all "groups" as the term is used herein. X and Y can be the same or different, and can be any groups capable of bonding in any way with the oligomeric thiocarbonate structural unit, whether ionically, covalently, or associatively. Both X and Y together can represent a single polyvalent species, such as a metal ion in a complex or an organic group to which the oligomeric thiocarbonate unit is attached as part of a ring structure. Preferably, X and Y are separate groups.

X and Y can be organic radicals. As used herein throughout the specification and the claims, the term "organic radical" means any radical which contains at least one carbon atom. An organic radical can be derived from an aliphatic, alicyclic, or aromatic compound, and can include straight chain, branched chain, and cyclic structures. An organic radical can be, for example, a substituted or unsubstituted alkyl, alkenyl, alkynyl, aryl, arylalkyl, or alkylaryl group, and can include heteroatoms such as oxygen, sulfur, nitrogen, and phosphorus. An organic radical can be joined to the oligomeric thiocarbonate structural unit at a carbon atom, e.g., a carbon atom of an alkyl group, or at a heteroatom contained in the organic radical, e.g., an oxygen atom of an alkoxy group, a nitrogen atom of an amino group, or a sulfur atom of a mercapto group; and typically is joined with a covalent bond. Typically, the organic radical comprises from 1 to about 100 carbon atoms, e.g., from 1 to about 50 carbon atoms, preferably from 1 to about 20 carbon atoms. More preferably, the organic radical is a hydrocarbyl group having from 1 to about 8 carbon atoms, such as methyl, ethyl, n-propyl, n-butyl, sec-butyl, t-butyl, hexyl, octyl, phenyl, and benzyl, and even more preferably an alkyl group having from 1 to about 4 carbon atoms.

Organic cations, i.e., organosubstituted heteroatomic cations, are preferred groups for X and Y. These can be represented by the general formula

wherein each of the four R groups independently is hydrogen or an organic radical, preferably a hydrocarbyl organic radical, with at least one R being an organic radical; and Q is a nonmetal, semi-metal or metalloid. Each R group typically has from 1 to about 50 carbon atoms, preferably from 1 to about 24 carbon atoms, with the total number of carbon atoms in all four R groups preferably being a maximum of about 60. Q is preferably nitrogen, phosphorus, arsenic, or antimony. These cations include, for example, primary, secondary, tertiary, and quaternary ammonium, phosphonium, arsonium, and stibonium cations; the quaternary cations are preferred; and quaternary ammonium cations are most preferred.

X and Y can also be inorganic groups. The term "inorganic group" as used herein throughout the specification and the claims means any group which contains no carbon atoms, and is intended to include metals, semi-metals, and metalloids as well as nonmetals such as the halogens, hydrogen, sulfur, nitrogen, and oxygen. Suitable inorganic groups include metals, typically in the form of cations, including alkali metals such as sodium and potassium, alkaline earth metals such as calcium, barium, and strontium, and transition metals such as iron, copper, nickel, zinc, lead, and cadmium; and ammonium ion.

Each —$CS_3$— subunit of the oligomeric structural unit corresponds to and comprises one mol of bound carbon disulfide. An oligomeric thiocarbonate compound thus comprises at least two mols of bound carbon disulfide, and may comprise a higher number, e.g., three, four, five, or six mols of bound carbon disulfide. The term "bound carbon disulfide" as used in the specification and the claims means carbon disulfide that is part of a —$CS_3$— subunit, as distinguished from unreacted carbon disulfide that may also be associated with an oligomeric thiocarbonate compound by solvation, for example. Each mol of bound carbon disulfide in the oligomeric thiocarbonate can be released as free carbon disulfide by decomposition of the oligomeric thiocarbonate. The bound carbon disulfide can be released all at once, for example by treating the oligomeric compound with a strong acid such as hydrochloric acid. Under some conditions, the bound carbon disulfide can be released incrementally. For example, certain water-soluble thiocarbonate dimers, e.g., tetramethylammonium and tetraethylammonium hexathiodicarbonates, can partially decompose in aqueous solution to release one mol of $CS_2$, leaving tri- or tetrathiocarbonates in solution, which can further decompose at a later time to release a second mol of $CS_2$. The incremental release of carbon disulfide can be advantageous for achieving prolonged pesticidal activity with the use of oligomeric thiocarbonates.

The present invention also provides processes of making certain oligomeric thiocarbonates. In one embodiment, an oligomeric thiocarbonate is made by reaction of sulfur, carbon disulfide, hydrogen sulfide, and a strong hydroxide base having a bulky cation. Alternatively, these oligomeric thiocarbonates can be made by reaction of sulfur, carbon disulfide, and a sulfide that can be regarded as the reaction product of hydrogen sulfide and such a base.

Proper selection of the base (or the corresponding sulfide) is critical to the formation of an oligomeric thiocarbonate in accordance with the novel processes of this invention. The base must be a strong hydroxide base ZOH (or corresponding sulfide $Z_2S$) having a bulky cation Z, preferably a cation at least as bulky as a tetramethylammonium ion. Bases with smaller cations, such as sodium hydroxide and potassium hydroxide, react to produce only monomeric thiocarbonates, e.g., tetrathiocarbonates, rather than the oligomeric thiocarbonates, e.g., hexathiodicarbonates (dimer thiocarbonates) made in accordance with the processes of this invention. Quaternary ammonium hydroxides are preferred bases. One class of quaternary ammonium hydroxides can be represented by the general formula

wherein each of the four R groups independently is an organic radical, preferably a hydrocarbyl organic radical, more preferably an alkyl, aralkyl, or aryl radical, typically having from 1 to about 50 carbon atoms, and preferably from 1 to about 24 carbon atoms. Preferably, the four R groups together have a total of at least 5 carbon atoms, typically from 5 to about 60 carbon atoms, more preferably from 5 to about 20 carbon atoms. Preferred R groups include methyl, ethyl, n-propyl, isopropyl, n-butyl, isobutyl, sec-butyl, t-butyl, benzyl, and phenyl groups.

Oligomeric thiocarbonates function as fumigants principally by decomposing to release carbon disulfide, a volatile, active toxicant. In addition, quaternary ammonium ions have independent biocidal effectiveness, particularly against microorganisms such as bacteria, algae, and fungi. The presence in a quaternary ammonium ion of at least one higher aliphatic, preferably alkyl, group having at least about 12 carbon atoms enhances the biocidal activity of the ion. Thus, oligomeric thiocarbonate compositions comprising higher alkyl substituted quaternary ammonium ions are preferred when such microorganisms are to be controlled. In this embodiment of the invention, at least one, preferably the largest, of the four R groups is an alkyl group having at least about 12 carbon atoms, and more preferably, when all of the R groups are aliphatic, between about 16 and about 18 carbon atoms. The presence of an aralkyl group such as a benzyl group in combination with a higher alkyl group even further enhances the biocidal activity of a quaternary ammonium ion. When at least one of the R groups is an aralkyl group such as benzyl, the largest R group is preferably an alkyl group having between about 12 and about 16 carbon atoms.

Many suitable quaternary ammonium hydroxides and salts, from which hydroxides can be prepared, for example by ion exchange, are commercially available. Specific examples of useful quaternary ammonium hydroxides include tetramethyl-, ethyltrimethyl-, methylethylphenylbenzyl-, methylethylpropylbutyl-, trimethyloctadecyl-, dimethyldioctadecyl-, trimethyltallow-, trimethylsoya-, trimethylcoco-, dimethyldicoco-, dimethyldi(hydrogenated tallow)-, trimethyldodecyl-, trimethylhexadecyl-, trimethylbenzyl-, dimethyldodecylbenzy-, dimethyltetradecylbenzyl-, dimethylhexadecylbenzyl-, dimethyloctadecylbenzyl-, methylbis(2-hydroxyethyl)coco-, methylpolyoxyethylenecoco-, methylbis(2-hydroxyethyl)oleyl-, methylpolyoxyethyleneoleyl-, methylbis(2-hydroxyethyl)octadecyl-, methylpolyoxyethyleneoctadecyl-, n-dodecyltetradecyldimethylbenzyl-, n-tetradecylhexadecyldimethylbenzyl-, n-dodecyltetradecyldimethylbenzyl-, n-dodecyltetradecyldimethyldichlorobenzyl-, n-octadecyldimethylbenzyl-, and n-dodecyltetradecylhexadecyldimethylethylbenzylammonium hydroxides.

Another class of quaternary ammonium hydroxides useful in the practice of this invention consists of pentavalent nitrogen ring compounds in which the ring nitrogen also bears an organic radical, e.g., lauryl pyridinium hydroxide and hexadecyl pyridinium hydroxide.

Similarly, strong hydroxide bases comprising other bulky cations, such as quaternary phosphonium, arsonium, and stibonium ions, can be used. In addition, other hydroxides having large cations can be used, such as cesium hydroxide.

In one embodiment of the invention, a quaternary ammonium hexathiodicarbonate, for example, tetraethylammonium hexathiodicarbonate, is made by reacting the corresponding quaternary ammonium hydroxide, hydrogen sulfide, carbon disulfide, and elemental sulfur in a molar ratio of about 2 mols of the quaternary ammonium hydroxide, about 1 mol of hydrogen sulfide, about 2 mols of carbon disulfide, and about 1 gram-atom of sulfur. The hydroxide is usually used as an aqueous solution, preferably at least about 40 weight percent in concentration. The proportion of water in the reaction medium is preferably kept to a minimum because the product may be slightly soluble in water. The reaction proceeds quickly at room temperature with evolution of heat, and is desirably conducted in a closed vessel under inert atmosphere at atmospheric pressure with cooling to keep the temperature below the boiling point of the reaction mixture, i.e., below the boiling point of carbon disulfide, about 46° C. Lower and higher temperatures and pressures can be used if desired, provided the reaction mixture is kept between its freezing and boiling points. A yellow precipitate of quaternary ammonium hexathiodicarbonate forms immediately. Initially, the carbon disulfide and the aqueous hydroxide solution usually form separate liquid phases. When the carbon disulfide phase disappears, the reaction is substantially complete. The reaction mixture is allowed to cool and the precipitate is recovered in a centrifuge, washed with a higher aliphatic alcohol (that is, higher than ethanol, for example, isopropanol) and then ether or a volatile hydrocarbon, centrifuged after washing and dried by flash evaporation. Quaternary ammonium hexathiodicarbonates can be made in this way in yields of at least about 25 percent of theory, usually at least about 50 percent, often at least about 75 percent, and even more than about 85 percent of theory.

In another embodiment, the reactants are added simultaneously and continuously to a well stirred, cooled reactor. A product slurry is continuously withdrawn and passed through a series of continuous centrifuges, where it is sequentially centrifuged, washed with an aliphatic alcohol, centrifuged, washed with ether or volatile hydrocarbon, centrifuged, and finally recovered. The product is dried by flash evaporation. The solvents are recovered by standard techniques for purification and are reused.

In another embodiment, a quaternary ammonium trithiocarbonate is first produced. For example, it can be made by reaction of a quaternary ammonium hydroxide, hydrogen sulfide, and carbon disulfide in a molar ratio of about 2 to about 1 to about 1, following batch or continuous procedures such as those described above. The trithiocarbonate, preferably dissolved in water, is reacted with elemental sulfur. A hexathiodicarbonate is produced, rather than the tetrathiocarbonate that would be expected based on previously published information on thiocarbonate chemistry. The equation for this reaction is

$$2\ (R_4N)_2CS_3 + S \rightarrow (R_4N)_2(CS_3)_2 + (R_4N)_2S$$

wherein $R_4N$ represents any quaternary ammonium ion. The bis-quaternary ammonium sulfide so produced is then reacted with carbon disulfide to produce more quaternary ammonium trithiocarbonate, which is recycled through the process.

The processes of the invention are preferably carried out under an inert atmosphere, i.e., in the substantial absence of oxygen, to avoid oxidative degradation of the product. The reactions are exothermic, particularly steps involving the reaction of base with hydrogen sulfide, so that sufficient cooling should be provided to prevent excessive boiling of the reaction mixture. Any convenient temperatures and pressures can be used; at normal atmospheric pressure, temperatures in the range of about −10° to about 50° C. are ususally satisfactory. preferably, the temperature is maintained below about 10° C. during the most exothermic phase and is then raised somewhat, e.g., to between about 20° and 30° C., to promote completion of the reaction.

The processes specifically described above involve the use of quaternary ammonium compounds. However, corresponding hydroxides and trithiocarbonates containing phosphonium, arsonium, stibonium, and other suitable cations can also be used to produce the corresponding hexathiodicarbonates and higher oligomeric thiocarbonates.

Oligomeric thiocarbonates prepared as described above can then be converted to other oligomeric thiocarbonates of this invention. Usually, the conversion is carried out under non-oxidizing conditions, since it appears that the oligomeric thiocarbonate structural unit is sensitive to oxidative degradation.

One conversion method is ion exchange. For example, a cation-exchange resin is charged with the desired cation, such as an alkali metal, alkaline earth metal, transition metal, ammonium, organosubstituted ammonium, organosubstituted phosphonium, organosubstituted arsonium, or organosubstituted stibonium ion, and a solution of a quaternary ammonium oligomeric thiocarbonate in water is passed through a column of the charged resin.

Many ion exchange materials are available commercially. These include inorganic materials such as mineral zeolites (for example, sodalite and clinoptilolite), the greensands, and clays (for example, the montmorillonite group), and synthetic products such as the gel zeolites, the hydrous oxides of polyvalent metals (for example, hydrated zirconium oxide), and the insoluble salts of polybasic acids with polyvalent metals (such as zirconium phosphate). Synthetic organic cation-exchange resins include weak-acid types based primarily on acrylic or methacrylic acid that has been cross-linked with a difunctional monomer such as divinylbenzene, and strong-acid types based primarily on sulfonated copolymers of styrene and divinylbenzene. Synthetic organic anion-exchange resins of varying base strengths are based on primary, secondary, and tertiary amine functionality incorporated into a variety of polymers, including epichlorohydrin-amine condensates, acrylic polymers, and styrene-divinylbenzene copolymers. Usually, cation-exchange materials will be employed when it is desired to replace the cation, e.g., the quaternary ammonium cation, used in the preparation of an oligomeric thiocarbonate with another cation.

The stability of oligomeric thiocarbonate compositions, whether solids, solutions, or suspensions, can be enhanced by the presence of sulfide and/or polysulfide. Stabilized oligomeric thiocarbonate compositions are less prone to premature decomposition and release of free carbon disulfide. Suitable sources of sulfide can be represented by the formula

$M_nS_x$ wherein M is selected from ammonium, alkali and alkaline earth metals, and organosubstituted heteroatomic cations; n is 2 when M is monovalent and 1 when M is divalent; and x is at least 1, usually from 1 to about 5. Suitable sources include, for example, ammonium, sodium, potassium, and calcium sulfides and polysulfides; organosubstituted ammonium, phosphonium, arsonium, and stibonium sulfides, e.g., bis-quaternary ammonium sulfides, and combinations thereof. Typically, the composition comprises at least about 0.01 equivalent (0.005 mol) of sulfide per mole of oligomeric thiocarbonate, preferably at least about 0.02 equivalent per mol, more preferably at least about 0.04 equivalent per mol, and even more preferably at least about 0.08 equivalent per mol. Much higher proportions of sulfide can be present without loss of stability, even as much as 10 equivalents or more of sulfide per mol of oligomeric thiocarbonate, preferably less than about 1 equivalent per mol, more preferably less than about 0.5 equivalent per mol. However, the higher proportions of sulfide can be useful when it is desired to introduce additional sulfur into soil in addition to fumigating it. Sulfide can be introduced at the time the oligomeric thiocarbonate is made, for example by including appropriate proportions of base and hydrogen sulfide in excess of the stoichiometric amount required to form the oligomeric thiocarbonate. Since thiocarbonates tend to decompose in the presence of acid, preferably sufficient base is used to neutralize the hydrogen sulfide. Alternatively, a source of sulfide can be admixed with the oligomeric thiocarbonate after it is made, for example when it is being made up into a formulation suitable for application, e.g., pellets, powder, solution, or suspension.

An excess of base is also beneficial in stabilizing the oligomeric thiocarbonates. Suitable bases include ammonium and alkali metal hydroxides, and hydroxide bases comprising organosubstituted heteroatomic cations, e.g., organosubstituted ammonium, phosphonium, arsonium, and stibonium ions. Quaternary ammonium hydroxides are preferred. Generally, the amount of added base will correspond to about 0.01, usually about 0.02, preferably at least about 0.04, and most preferably at least about 0.08 equivalents of base per mole of oligomeric thiocarbonate.

Any amount of added base, sulfide, or polysulfide enhances the stability of the oligomeric thiocarbonates. Combinations of the described bases, sulfides, and/or polysulfides can be used to further enhance stability and are presently preferred. Presently, the most preferred stabilized oligomeric thiocarbonate compositions contain added base in addition to one or more of the described sulfides or polysulfides.

Oligomeric thiocarbonates, e.g., bis(tetramethylammonium) hexathiodicarbonate, can be made in accordance with this invention essentially free of solvation by carbon disulfide, i.e., free of carbon disulfide present by solvation.

Compositions comprising oligomeric thiocarbonates can be used as agricultural biocides in any application where tri- and tetrathiocarbonates can be used, as described, for example, in U.S. Pat. Nos. 4,476,113, 4,551,167, and 4,726,144. They can be used for the control of a wide variety of plant and animal pests, including insects, rodents, fungi, nematodes, acarids, bacteria, arachnids, gastropods, and worms. They can be used in or on soil and as aerial plant pesticides for topical treatment of trees or crops. At higher application rates, they can also be used as herbicides for the control of undesirable plants.

Such compositions can be formulated in many ways for various applications in agricultural practice. They can be formulated, for example, as powders or wettable powders, alone or admixed with carriers, extenders, coatings, and other additives; as crystalline solids; as compressed pellets, alone or with binders; and in liquid medium, that is, as suspensions or solutions in water or organic liquids such as oils or solvents.

Oligomeric thiocarbonates have several advantages over the tri- and tetrathiocarbonates. They are not appreciably hygroscopic, they are less subject to oxidation in air, and they are more stable when in contact with a dry substrate such as dry foliage or soil. They can be made soluble or substantially insoluble in water, for best results in different applications. For example, tetraalkylammonium hexathiodicarbonates in which the tetraalkylammonium ions have a total of less than about 16 carbon atoms, preferably no more than about 12 carbon atoms, are soluble to a useful degree in water. Those in which the tetraalkylammonium ions have 16 or more carbon atoms have low solubility and thus are more stable in the presence of moisture.

Thus, oligomeric thiocarbonates can be applied to the aerial portions of plants, e.g., foliage, stems, fruit, or tree trunks, as a dry powder or a suspension in a non-aqueous, nonsolvent liquid carrier such as an oil, and will retain their pesticidal activity for a substantial length of time, providing prolonged protection against fungal and bacterial infection and acting as a contact pesticide against animal pests of all kinds.

Soil application of an oligomeric thiocarbonate composition can be accomplished either prior to planting or after plant growth is established. It should be noted, however, that different plant species exhibit differing tolerances to chemical agents. In addition, the phytotoxicity of a chemical agent to a particular plant can be dependent upon its growth stage. Germination is not inhibited for most plant seeds after soil treatment, and growth of established plants is usually not significantly altered. Some seedlings can show phytotoxicity symptoms.

The compositions can be applied in liquid medium by spraying onto the soil surface. Injection into the soil, using a shank or knife, is also a useful method for applying the compositions. This application can either be "flat," wherein the injectors are closely spaced to treat essentially the entire field area, or can be "localized" by spacing the injectors such that only the plant growing bed is treated, in bands. Similarly, solid compositions can be broadcast on the soil or, preferably, distributed in trenches or furrows and covered over with soil. The solid compositions can also be applied in a localized manner near the root zone of crops or trees, for example around trees under the drip line. Because the oligomers are stable in contact with dry soil, they can be applied to the soil and allowed to remain until the soil is irrigated, either by natural rainfall or by artificial means such as sprinkler or flood irrigation. The irrigation water will move the composition into the soil and promote the release of carbon disulfide, the actual fumigant. At the same time, the water slows the diffusion of the carbon disulfide from the soil into the air, and thus prolongs contact between the carbon disulfide and soil pests.

Oligomeric thiocarbonates are effective as soil fumigants over a wide range of application rates. The particular application rate for a particular situation depends on many factors, such as the pest or pests to be controlled, the crop to be protected and its state of growth, soil moisture and other conditions, and the like. Generally, the compositions provide beneficial effects at application rates as low as about 1 pound, preferably at least about 5 pounds, of releasable carbon disulfide content per acre of soil treated, and as high as about 2000 pounds, usually less than about 1000 pounds, $CS_2$ per acre. Typically, for the overall fumigation of cultivated fields, the compositions are applied at rates of from about 10 to about 500 pounds, preferably less than about 250 pounds, more preferably less than about 125 pounds, and most preferably from about 15 to about 75 pounds, $CS_2$ per acre. If the compositions are applied in a localized manner, for example under the drip lines of trees, the effective application rate can be much higher than the average per acre, since only the soil in the root zones is actually treated.

Another example of soil application is in the planting of trees, or the replacement of diseased or dead trees, in an orchard. When the planting hole is dug or the old tree is removed, an oligomeric thiocarbonate composition can be mixed with the loose soil from the hole, which is then placed around the roots of the new tree. This controls pests in and around the planting hole and provides a healthier environment for the new tree to become established.

The oligomeric thiocarbonates can be combined with other agricultural chemicals to provide a multifunctional product. For example, they may be combined with solid or liquid fertilizers such as urea, ammonia, ammonium nitrate, calcium nitrate, etc. and other sources of plant nutrients. Since the described thiocarbonates inhibit nitrification, they reduce the rate at which ammoniacal compounds, such as fertilizers, are nitrified in the soil. Ammoniacal fertilizers are well known in the art, and as that term is used herein, it includes ammonia and ammonium-containing compounds as well as ammonia and ammonium compound formers such as urea, biuret, etc. Illustrative ammonium-containing compounds include ammonium nitrate, ammonium sulfate, etc.

The compositions also can be used in non-soil fumigation procedures, such as in the chamber fumigation of commodities which are introduced into commerce. In this type of procedure, acidification of a composition or the application of heat, or both, can be used to promote a rapid decomposition into the fumigant components. Upon termination of the fumigation procedure, vapors in the chamber can be drawn through a scrubbing system, e.g., one containing an alkaline aqueous solution, to remove the fumigant and prevent atmospheric pollution when the chamber is opened.

Oligomeric thiocarbonate compositions are also useful for the preservation of cellulosic materials stored in bulk. Such materials, for example, silage, wood chips, animal feed, grain, hay, straw, and the like, are often stored for considerable periods of time in bulk under less than ideal conditions. Residual moisture in the materials, ground moisture, and rain can promote the growth of molds, fungi, and bacteria. Heat generated by the growth of those organisms, as well as metabolic activity of surviving cells of the stored material, further accelerates the deterioration of the material. Substantial loss of valuable constituents and total biomass of the stored material often results. Treating such materials with an oligomeric thiocarbonate, such as a quaternary ammonium hexathiodicarbonate, can inhibit the metabolic activity and growth of organisms that contribute to the loss. A fumigant composition can be applied simply by spraying into the product as it is being transported to the storage enclosure with a conveyor, auger or other device. The composition can be applied to agricultural products which are already in storage, by spraying onto the exposed products and sealing the storage enclosure. Preferably, when the material is stored outdoors (e.g., wood chips), the thiocarbonate composition is applied as a suspension in a light hydrocarbon or mineral oil, which enhances the dispersion of the thiocarbonate throughout the mass, and provides some measure of protection against loss of thiocarbonate due to rain. Usually, the oligomeric thiocarbonate is applied at the rate of at least about 0.1 pound of releasable $CS_2$ content per dry ton of stored material (0.05 kg per metric ton), preferably between about 0.3 and about 5 pounds per ton (between about 0.15 kg and about 2.5 kg per metric ton).

It is also possible to use the thiocarbonate compositions for fumigating rooms or storage enclosures; this is accomplished by spraying the floor and walls with the composition, and sealing the space until the desired fumigation is accomplished. As an alternative to spraying, a technique similar to chamber fumigation can be used, wherein heat decomposes the composition in an enclosed space.

The fumigating property of compositions described herein has been expressed primarily in terms of the available carbon disulfide content. It should be noted, however, that other components can contribute to efficacy as a pesticide. Quaternary ammonium ion, for example, is widely employed for disinfecting and algicidal purposes. In addition, sulfur is very widely used as a combination fungicide, acaricide, and insecticide, so any of the compositions of the invention which decompose to form sulfur will have similar properties in addition to the properties attributable to the carbon disulfide content.

The invention is further described by the following examples, which are illustrative of various aspects of the invention and are not intended as limiting the scope of the invention as defined by the appended claims.

EXAMPLE 1

To a three-neck flask containing 150.0 g of 40 weight percent aqueous tetraethylammonium hydroxide (0.408 mol) was added 6.85 g (0.214 mol) of sulfur powder and 6.94 g (0.204 mol) of hydrogen sulfide gas. The solution, which warmed slightly, was stirred to dissolve the sulfur. Then 32.56 g (0.428 mol) of carbon disulfide was added dropwise with moderate stirring and cooling to maintain the temperature at or below 40° C. During cooling to room temperature, an orange solid precipitated. The reaction mixture was then cooled to 0° C., and the solid was isolated by filtration, washed twice with cold isopropyl alcohol, twice with ethyl ether, and dried. The product was crystalline and free-flowing. The yield was 85.9 g, about 88.5 percent based on a molecular weight of 476.

The crystals appeared to become only slightly less free-flowing on standing overnight on a watch glass at 50 percent relative humidity.

Upon decomposition in acid, and collecting carbon disulfide in toluene, it was found that the solid contained 29.5 weight percent carbon disulfide. The nominal carbon disulfide contained in monomeric tetraethylammonium tetrathiocarbonate [$(C_2H_5)_4N]_2CS_4$, molecular weight 400, is 19 weight percent. The nominal carbon disulfide contained in the dimer, tetraethylammonium hexathiodicarbonate $(C_2H_5)_4NCS_3CS_3N(C_2H_5)_4$, molecular weight 476, is 31.9 percent.

EXAMPLE 2

In this example, tetramethylammonium hydroxide, hydrogen sulfide, sulfur, and carbon disulfide are reacted in a molar ratio of 2:1:4:4 to produce an oligomeric thiocarbonate comprising 4 mols of bound carbon disulfide:

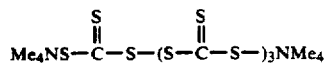

To a bottle containing 12.32 g (0.068 mol) of solid tetramethylammonium hydroxide pentahydrate and 4.35 g (0.136 mol) of sulfur powder was added 1.16 g (0.034 mol) of gaseous hydrogen sulfide. The solid base became liquid upon addition of the hydrogen sulfide and almost all the sulfur dissolved. In one portion was added 10.34 g (0.136 mol) of carbon disulfide, which formed a second liquid phase. The mixture was shaken for 30 minutes. After about 15 minutes, there was no apparent free carbon disulfide; that is, the second liquid phase had disappeared. The mixture became almost solid with orange precipitate. The mixture was chilled, and the solid was filtered on a sintered glass crucible, during which it became darker and redder. It was held under vacuum in a dessicator with concentrated sulfuric acid drying agent overnight. The product was a dark red viscous solid with amine odor, which showed no evident tendency to be hygroscopic. The viscous solid was made free-flowing by the addition of 35 weight percent calcium hydroxide and triturating with a spatula. The product was presumed to be $(CH_3)_4N(CS_3)_3(CS_4)N(CH_3)_4$, molecular weight 612, theoretical carbon disulfide content 49.7 weight percent. The measured $CS_2$ content was 25-26 weight percent.

When an alkali metal hydroxide is used as the base, the product is the alkali metal tetrathiocarbonate, and only one mol of carbon disulfide and one gram-atom of sulfur are consumed per two mols of base and one mol of hydrogen sulfide. The excess carbon disulfide and sulfur remain as a clearly visible second phase. Thus it is surprising that, when a quaternary ammonium hydroxide is used as the base, all of the excess carbon disulfide and sulfur are consumed as shown in this example. Although the analytical result above did not confirm the formation of an oligomer containing four mols of bound carbon disulfide, it is not inconsistent with the formation of a product mixture comprising such an oligomer.

EXAMPLE 3

In several screening tests, tetraethylammonium hexathiodicarbonate has shown a higher degree of efficacy against nematodes and fungi than a solution of sodium tetrathiocarbonate in water having the same releasable carbon disulfide content.

Test 1

Six-inch diameter pots, each containing 1800 g of sandy soil with a growing tomato plant, received 1500 larvae each of root-knot nematode, *Meloidogyne incognita*, injected uniformly around the tomato roots. Test chemical was added by trenching around the plant and covering with soil. Untreated controls received only water. All treatments were replicated 6 times. The tomatoes were grown 35 days, at which time the whole plants were harvested. The extent of root galling was indexed on a scale of 0 to 5, where 5 denoted that the root system was totally galled. The results are summarized in Table 1.

TABLE 1

| Treatment | Mean Galling Index |
|---|---|
| Control (water only) | 4.5 |
| $Na_2CS_4$ solution, | |
| 0.39 g $CS_2$/pot, 217 ppmw | 2.0 |
| 0.19 g $CS_2$/pot, 105 ppmw | 1.7 |
| $(Et_4N)_2C_2S_6$ powder, | |
| 0.17 g $CS_2$/pot, 94 ppmw | 0.8 |

TABLE 1-continued

| Treatment | Mean Galling Index |
|---|---|
| 0.09 g CS₂/pot, 50 ppmw | 0.9 |

Test 2

Sterilized test soil was uniformly infested with pythium, a water-mold. The soil was split into 6 replicates, 500 g each, in 1-liter beakers, and incubated 24 hours. A 200 g subsample from each beaker was then placed in an aluminum tray in a layer about ¼ inch deep. To each tray were added 20 ripe tomatoes, 120 in all, as bait for pythium. After 4 days, each tomato was inspected for a watery, rotted appearance at the area of contact with soil. The results are presented in Table 2.

TABLE 2

| Treatment | % of Fruit Infected |
|---|---|
| Uninfested control | 0.0 |
| Infested, untreated | 16.7 |
| Na₂CS₄ solution, | |
| 100 ppmw CS₂/soil | 12.5 |
| 400 ppmw CS₂/soil | 20.0 |
| (Et₄N)₂C₂S₆ powder, | |
| 100 ppmw CS₂/soil | 6.7 |
| 400 pmw CS₂/soil | 7.5 |

Test 3

Sterilized test soil was uniformly infested with phytophthora, a water-mold. The soil was split into 500 g (dry weight basis) portions in 1-liter beakers Treatments were added to the beakers by opening 4 holes in a uniform pattern, adding test chemical evenly among the holes, and closing completely. Treatments were replicated 6 times. The treated soils were incubated 24 hours, at which time each was mixed thoroughly. Three equal subsamples from each were placed in aluminum trays in layers about ¼ inch deep. To each tray were added 12 green tomatoes as bait for phytophthora. After 2 and 3 days, each tomato was inspected for brown spots, a symptom of infection. From the number of spotted tomatoes the disease incidence (% of fruit) was calculated. In addition, after 4 days, the average percentage of fruit surface browned was estimated, and presented as disease severity (% of surface area). The results are presented in Table 3.

TABLE 3

| Treatment | Disease Incidence | | Disease Severity |
|---|---|---|---|
| | Day 2 | Day 3 | |
| Untreated, | | | |
| uninfested | 0 | 0 | 0 |
| infested | 100 | 100 | 79 |
| Na₂CS₄ solution | | | |
| 100 ppmw CS₂/soil | 100 | 100 | 72 |
| 400 ppmw CS₂/soil | 22 | 100 | 54 |
| (Et₄N)₂C₂S₆ | | | |
| 100 ppmw CS₂/soil | 56 | 100 | 37 |
| 400 ppmw CS₂/soil | 11 | 77 | 12 |

The oligomeric thiocarbonate was more effective than sodium tetrathiocarbonate, on an equivalent CS₂ basis, in reducing the incidence and/or severity of the infection.

While particular embodiments of the invention have been described, it will be understood, of course, that the invention is not limited thereto, since many obvious modifications can be made, and it is intended to include within this invention any such modifications as will fall within the scope of the appended claims.

Having now described the invention, we claim:

1. A method for controlling animal and fungal pests which comprises applying to an area in which said pests are to be controlled less than a herbicidal amount of an oligomeric thiocarbonate represented by the formula

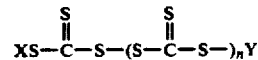

wherein n is at least 1 and X and Y independently are inorganic cations selected from the group consisting of alkali metal cations, alkaline earth metal cations, and transition metal cations or organic cations consisting of

wherein each of $R_5$, $R_6$, $R_7$, and $R_8$ is independently an organic radical selected from the group consisting of alkyl radicals, aralkyl radicals, and aryl radicals, said alkyl radicals, aralkyl radicals, and aryl radicals having from 1 to about 10 carbon atoms, for a total of between 5 and 20 carbon atoms.

2. The method defined in claim 1 wherein said thiocarbonate is applied to soil in which plant growth is established.

3. The method defined in claim 1 wherein said thiocarbonate is applied to soil which contains ungerminated plant seeds.

4. The method defined in claim 1 wherein said thiocarbonate is applied in combination with a nitrogenous fertilizer.

5. The method defined in claim 4 wherein said nitrogenous fertilizer comprises urea.

6. The method defined in claim 1 wherein said pests are selected from the group consisting of bacteria, fungi, insects, rodents, gastropods, arachnids, worms, nematodes and combinations thereof.

7. A method for providing an oligomeric thiocarbonate fumigant to a space control animal and fungal pests comprising:

applying to said space less than a herbicial amount of an oligomeric thiocarbonate, said thiocarbonate represented by the formula

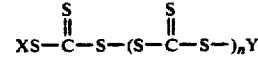

wherein n is at least 1 and X and Y independently are inorganic cations, consisting of

wherein each of $R_5$, $R_6$, $R_7$, and $R_8$ is independently an organic radical selected from the group consisting of alkyl radicals, aralkyl radicals, and aryl radicals, said alkyl radicals, aralkyl radicals, and aryl radicals having from 1 to about 10 carbon atoms, for a total of between 5 and 20 carbon atoms, or an inorganic cation selected from the group consisting of alkali metal cations, alkaline earth metal cations, and transition metal cations, to produce at least some carbon disulfide within said space.

8. The method of claim 7 wherein said pests are selected from the group consisting of bacteria, fungi, insects, rodents, gastrophods, arachnids, worms, and nematodes.

9. A method for controlling animal and fungal pests in soil which comprises applying to the soil a less than a herbicial amount of a thiocarbonate composition represented by the formula

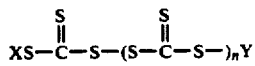

wherein n is at least 1 and X and Y independently are organic cations, consisting of

wherein each of $R_5$, $R_6$, $R_7$, and $R_8$ is independently an organic radical selected from the group consisting of alkyl radicals, aralkyl radicals, and aryl radicals, said alkyl radicals, aralkyl radicals, and aryl radicals having from 1 to about 10 carbon atoms, for a total of between 5 and 20 carbon atoms, or an inorganic cation selected from the group consisting of alkali metal cations, alkaline earth metal cations, and transition metal cations, which tihocarbonate composition comprises more than one mole of bound carbon disulfide.

10. The method defined in claim 9 wherein said thiocarbonate is applied by injecting in liquid medium into the soil.

11. The method defined in claim 9 wherein said thiocarbonate is applied as a solid beneath the surface of the soil.

12. A method as defined in claim 9 wherein said thiocarbonate is applied as an admixture with a nitrogenous fertilizer.

13. The method defined in claim 12 wherein said nitrogenous fertilizer comprises urea.

14. The method as defined in claim 9 wherein the thiocarbonate composition comprises substantially more than one mol of bound carbon disulfide.

15. The method defined in claim 9 wherein X and Y independently are selected from the group consisting of inorganic cations.

16. The method defined in claim 9 wherein n is 1.

17. A method for controlling nematodes which comprises applying a nematodicidally effective, but less than herbicidal amount of an oligomeric thiocarbonate represented by the formula

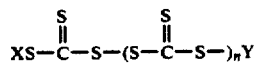

wherein n is at least 1 and X and Y independently are inorganic cations selected from the group consisting of alkali metal cations, alkaline earth metal cations, and transition metal cations or organic cations consisting of

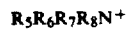

wherein each of $R_5$, $R_6$, $R_7$, and $R_8$ is independently an organic radical selected from the group consisting of, alkyl radicals, aralkyl radicals, and aryl radicals, each of said alkyl radicals, aralkyl radicals, and aryl radicals having from about 1 to about 10 carbon atoms, for a total of between 5 and 20 carbon atoms to an area in which nematodes are to be controlled.

18. The method as defined in claim 17 wherein said thiocarbonate is applied by spraying in liquid medium onto the soil.

19. The method defined in claim 17 wherein said thiocarbonate is applied by injecting in liquid medium into the soil.

20. The method defined in claim 17 wherein said thiocarbonate is applied as a solid beneath the surface of the soil.

21. The method defined in claim 17 wherein said thiocarbonate comprises a compound where n is equal to one.

22. The method defined in claim 17 wherein said thiocarbonate is applied to soil containing ungerminated plant seeds.

23. The method defined in claim 17 wherein said thiocarbonate is applied to soil in which plant growth is established.

24. The method defined in claim 17 wherein n is 1.

25. A method for preserving cellulosic material against attack from animal and fungal pests which comprises applying to the material less than a herbicidal amount of an oligomeric thiocarbonate represented by the formula

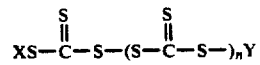

wherein n is at least 1 and X and Y independently are inorganic cations selected from the group consisting of alkali metal, alkaline earth metal, and transition metal cations, or organic cations consisting of:

wherein each of $R_5$, $R_6$, $R_7$, and $R_8$ is independently an organic radical selected from the group consisting of alkyl radicals, aralkyl radicals, and aryl radicals, each of said alkyl radicals, aralkyl radicals, and aryl radicals having from about 1 to about 10 carbon atoms, for a total of between 5 and 20 carbon atoms.

26. The method defined in claim 25 wherein the cellulosic material is selected from the group consisting of silage, wood chips, animal feed, grain, hay, and straw.

27. The method defined in claim 25 wherein the thiocarbonate comprises a compound where n is equal to one.

28. The method defined in claim 27 wherein n equals one.

29. The method defined in claim 1 wherein the oligomeric thiocarbonate is applied to an aerial portion of a plant.

30. The method defined in claim 29 wherein n equals one and O+ is N+.

31. The method defined in claim 29 wherein the thiocarbonate comprises a compound where X and Y independently comprise

wherein each of $R_5$, $R_6$, $R_7$, and $R_8$ is independently an organic radical selected from the group consisting of alkyl radicals, aralkyl radicals, and aryl radicals, each of said alkyl radicals, aralkyl radicals, and aryl radicals having from about 1 to about 10 carbon atoms, for a total of between 5 and 20 carbon atoms.

32. The method defined in claim 30 wherein the thiocarbonate comprises a compound where X and Y independently comprise $$R_5R_6R_7R_8N^+$$

wherein each of $R_5$, $R_6$, $R_7$, and $R_8$ is independently an organic radical selected from the group consisting of alkyl radicals, aralkyl radicals, and aryl radicals, each of said alkyl radicals, aralkyl radicals, and aryl radicals having from about 1 to about 10 carbon atoms, for a total of between 5 and 20 carbon atoms.

33. A method for controlling pests selected from the group consisting of fungi, insects, rodents, gastrophods, arachnids, worms, nematodes and combinations thereof, which comprises applying to an area in which said pests are to be controlled less than a herbicidally effective amount, yet pesticidally effective amount of a hexathiodicarbonate represented by the formula $$XS-\overset{S}{\underset{\|}{C}}-S-S-\overset{S}{\underset{\|}{C}}-SY$$

wherein X and Y independently are selected from the group consisting of alkali metal, alkaline earth metal, transition metal, ammonium, and cations selected from the group consisting of cations independently comprising $$R_5R_6R_7R_8Q^+$$

wherein each of $R_5$, $R_6$, $R_7$, and $R_8$ is independently an organic radical selected from the group consisting of alkyl radicals, aralkyl radicals, aryl radicals, and hydrogen, each of said alkyl radicals, aralkyl radicals, and aryl radicals having from about 1 to about 10 carbon atoms, for a total of no more than between 5 and, and Q selected from the group consisting of nitrogen, phosphorous, arsenic, and antimony.

34. A method for controlling pests selected from the group consisting of fungi, insects, rodents, gastrophods, arachnids, worms, nematodes and combinations thereof, which comprises applying to an area in which said pests are to be controlled a pesticidally effective amount of a hexathiodicarbonate represented by the formula $$XS-\overset{S}{\underset{\|}{C}}-S-S-\overset{S}{\underset{\|}{C}}-SY$$

wherein X and Y independently are selected from the group consisting of cations containing organic radicals having from 1 to about 20 carbon atoms.

* * * * *

UNITED STATES PATENT AND TRADEMARK OFFICE
CERTIFICATE OF CORRECTION

PATENT NO. : 5,288,753

DATED : February 22, 1994

INVENTOR(S) : James A. Green, II and Donald C. Young

It is certified that error appears in the above-identified patent and that said Letters Patent is hereby corrected as shown below:

Claim 7, column 14, line 42, after "space" insert -- to --.

Claim 7, column 14, line 54, replace "inorganic" with -- organic --.

Claim 9, column 15, line 5, replace "herbicial" with -- herbicidal --.

Claim 9, column 15, line 25, replace "tihocarbonate" with -- thiocarbonate --.

Claim 14, column 15, line 39, after "method" delete "as".

Signed and Sealed this

Sixteenth Day of May, 1995

Attest:

BRUCE LEHMAN

Attesting Officer     Commissioner of Patents and Trademarks